(12) United States Patent
Nishtala et al.

(10) Patent No.: US 8,187,291 B2
(45) Date of Patent: May 29, 2012

(54) DEVICE FOR CONTROLLED ENDOSCOPIC PENETRATION OF INJECTION NEEDLE

(75) Inventors: Srinivas Nishtala, Bloomington, IN (US); Tim E. Ward, Ellettsville, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 354 days.

(21) Appl. No.: 12/134,008

(22) Filed: Jun. 5, 2008

(65) Prior Publication Data

US 2008/0234695 A1    Sep. 25, 2008

Related U.S. Application Data

(63) Continuation of application No. 11/006,530, filed on Dec. 8, 2004, now Pat. No. 7,402,163, which is a continuation of application No. 10/459,615, filed on Jun. 12, 2003, now Pat. No. 6,843,792, which is a continuation of application No. 10/083,467, filed on Feb. 27, 2002, now Pat. No. 6,663,645, which is a continuation of application No. 09/192,591, filed on Nov. 17, 1998, now Pat. No. 6,371,963.

(51) Int. Cl.
*A61B 17/32* (2006.01)

(52) U.S. Cl. ............... 606/167; 606/113; 606/139

(58) Field of Classification Search ............ 606/113, 606/114, 110, 167, 115, 185, 139, 205, 172, 606/200; 604/242, 103.03, 272, 117, 115, 604/164.01; 600/201, 562, 567, 117, 104
See application file for complete search history.

(56) References Cited

U.S. PATENT DOCUMENTS

| | | | |
|---|---|---|---|
| 2,137,710 A | 11/1938 | Anderson | |
| 4,222,380 A * | 9/1980 | Terayama | 604/115 |
| 4,830,002 A | 5/1989 | Semm | |
| 5,176,647 A * | 1/1993 | Knoepfler | 604/158 |
| 5,199,441 A * | 4/1993 | Hogle | 600/566 |
| 5,312,351 A | 5/1994 | Gerrone | |
| 5,356,416 A | 10/1994 | Chu et al. | |
| 5,376,094 A | 12/1994 | Kline | |
| 5,417,697 A | 5/1995 | Wilk et al. | |
| 5,542,948 A | 8/1996 | Weaver et al. | |
| 5,741,271 A | 4/1998 | Nakao et al. | |
| 5,746,747 A | 5/1998 | McKeating | |
| 5,792,164 A | 8/1998 | Lakatos et al. | |
| 5,846,248 A * | 12/1998 | Chu et al. | 606/114 |
| 5,871,470 A * | 2/1999 | McWha | 604/158 |
| 5,944,728 A | 8/1999 | Bates | |
| 5,947,978 A | 9/1999 | Holsinger | |
| 5,961,526 A | 10/1999 | Chu et al. | |
| 5,997,547 A | 12/1999 | Nakao et al. | |
| 6,007,546 A * | 12/1999 | Snow et al. | 606/113 |
| 6,120,476 A * | 9/2000 | Fung et al. | 604/95.04 |
| 6,139,541 A * | 10/2000 | Vanney et al. | 606/1 |
| 6,371,963 B1 | 4/2002 | Nishtala et al. | |
| 6,663,645 B2 | 12/2003 | Nishtala et al. | |
| 6,843,792 B2 | 1/2005 | Nishtala et al. | |

* cited by examiner

*Primary Examiner* — Ryan Severson
*Assistant Examiner* — Tin Nguyen
(74) *Attorney, Agent, or Firm* — Finnegan, Henderson, Farabow, Garrett & Dunner LLP

(57) ABSTRACT

An endoscopic needle device comprises a handle and a catheter sheath connected to the handle, wherein the catheter sheath has at least one lumen, for example a needle lumen and a stabilization lumen, extending therethrough. A needle is selectively movable within the needle lumen between a needle retracted position and a needle extended position and a stabilization element is selectively movable within the stabilization lumen between a stabilizer retracted position and a stabilizer extended position. A linking mechanism may operatively connect the needle and the stabilization element so that when the needle is in the needle retracted position the stabilization element is in the stabilizer extended position and when the needle is in the needle extended position the stabilization element is in the stabilizer retracted position.

15 Claims, 9 Drawing Sheets

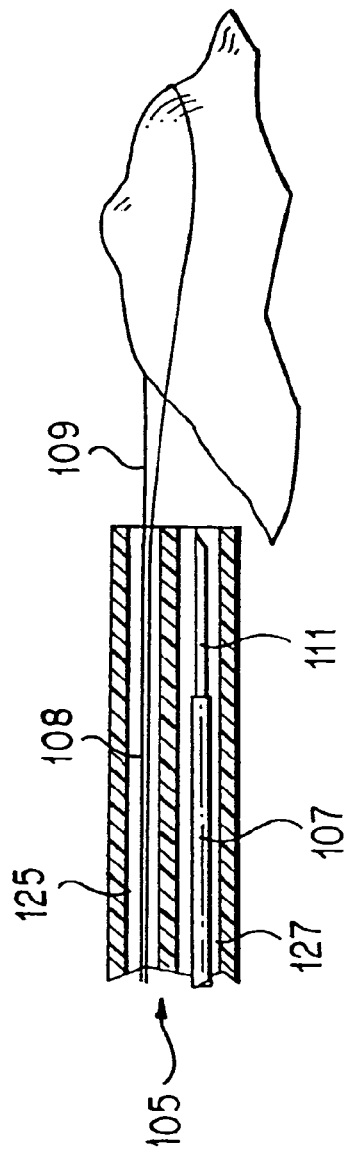
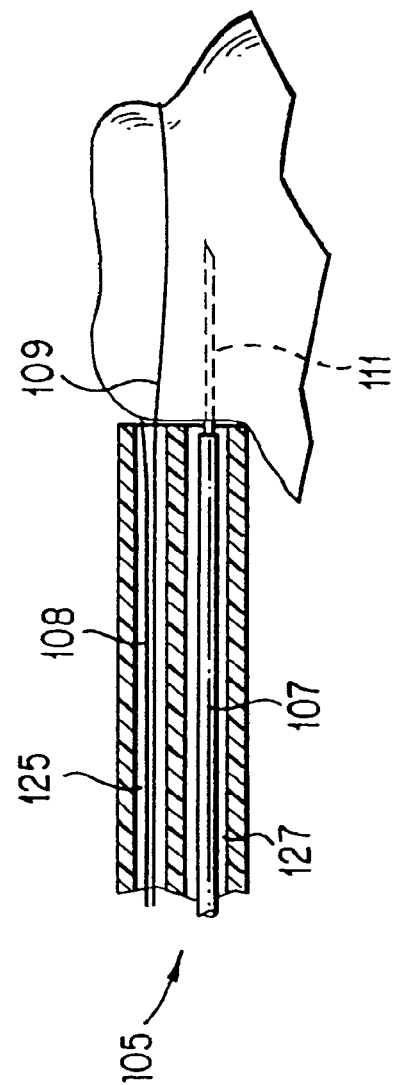

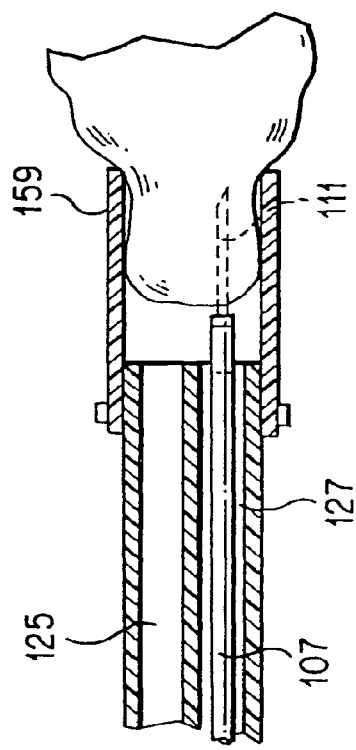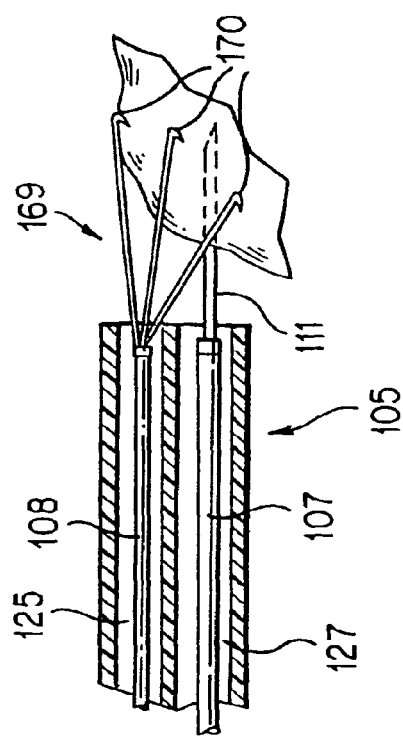

DEVICE FOR CONTROLLED ENDOSCOPIC PENETRATION OF INJECTION NEEDLE

RELATED APPLICATIONS

This application is a continuation of U.S. application Ser. No. 11/006,530 filed Dec. 8, 2004, now U.S Pat. No. 7,402,163, which is a continuation of U.S. application Ser. No. 10/459,615, filed Jun. 12, 2003, now U.S Pat. No. 6,843,792, which is a continuation of U.S. application Ser. No. 10/083,467, filed on Feb. 27, 2002, now U.S. Pat. No. 6,663,645, which is a continuation of U.S. application Ser. No. 09/192,591, filed Nov. 17, 1998, now U.S Pat. No. 6,371,963, which are incorporated herein in their entirety.

FIELD OF THE INVENTION

The present invention relates to endoscopic needle devices, and in particular relates to an endoscopic needle device allowing for controlled penetration of an injection needle.

BACKGROUND INFORMATION

Endoscopic needle devices are used for a variety of applications, including fine needle aspiration to collect cell cultures, injection sclerotherapy to stop bleeding, and sub-mucosal injection of saline for EMR imaging. Current endoscopic needle devices used for these and other purposes typically consist of an actuation handle, a flexible catheter sheath, and a rigid metal needle. While current endoscopic needles are generally adequate for penetration of soft tissues, known devices may have difficulty penetrating tough lesions and tumors. Because the application of force by the operator occurs outside the body, the force may not be entirely transferred to the injection site. Accordingly, the needle may be unable to apply enough pressure at the site to achieve penetration. Moreover, even if the needle does penetrate the site, the depth of penetration cannot be readily controlled. For known embodiments of endoscopic needle devices, this latter drawback exists for soft tissue penetration as well as for harder tissues.

In addition, many lesions, tumors, or other injection sites are relatively inaccessible or hard to reach. These sites may require some manipulation or stabilization of the intended site. Known endoscopic needle devices do not provide stabilization of the site to effect penetration in many situations, much less stabilization that would allow controlled penetration of the needle.

SUMMARY OF THE INVENTION

In an exemplary embodiment, the present invention is directed to an endoscopic needle device, comprising a handle and a catheter sheath connected to the handle, wherein the catheter sheath has at least one lumen extending therethrough. A needle is selectively movable within the lumen between a needle retracted position and a needle extended position and a stabilization element is selectively movable within the lumen between a stabilizer retracted position and a stabilizer extended position.

BRIEF DESCRIPTION OF THE DRAWINGS

FIG. 7 is a side view of a distal end of the endoscopic needle device of FIG. 1 at a penetration site, with the stabilization element of FIG. 1 in an extended position;

FIG. 8 is a side view of the distal end of the endoscopic needle device of FIG. 1 at a penetration site, with the stabilization element of FIG. 1 in a retracted position;

FIG. 11 is a side view of the endoscopic needle device of FIG. 9 being employed to penetrate a lesion;

FIG. 12 is a side view of a distal end of the endoscopic needle device of FIG. 1 including a fifth exemplary embodiment of a stabilization element according to the present invention.

DETAILED DESCRIPTION OF THE INVENTION

Figure 1:
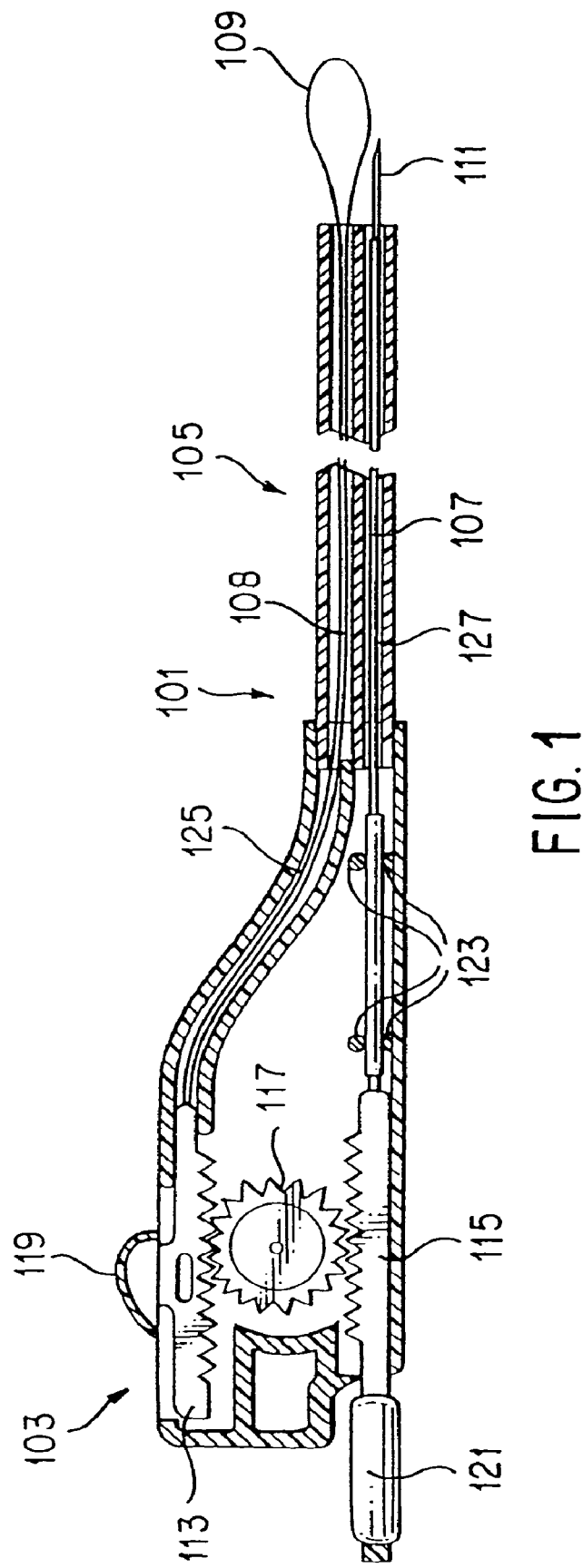
FIG. 1 is a side view of an exemplary embodiment of an endoscopic needle device according to the present invention, including a first exemplary embodiment of a stabilization element according to the present invention.

FIG. 1 illustrates an exemplary endoscopic needle device 101 according to the present invention. The needle device 101 includes, for example, a handle 103 connected to a catheter sheath 105 (the term catheter sheath is intended to include any sort of catheter or similar tubular member). The catheter sheath 105, which extends from a proximal end coupled to the handle 103 to a distal end, will typically be a flexible member, but may be completely or partially rigid if suitable. The catheter sheath 105 has at least one lumen extending therethrough. In the exemplary embodiment of FIG. 1, the catheter sheath 105 includes, for example, a pair of lumens extending axially therethrough, a needle lumen 127 and a stabilization lumen 125. The needle lumen 127 and stabilization lumen 125 terminate at openings located, for example, at the distal end of the catheter sheath 105 (the distal end being located to the right in each of the Figures).

A needle 107 extends, for example, through the needle lumen 127 from a needle base 115 disposed in the handle 103, to a needle head 111 which, in an extended position, protrudes from the distal end of the needle lumen 127. In a retracted position, the needle head 111 may be completely received within the needle lumen 127. A needle hub 121 may also be attached to the needle 107 at, for example, the needle base 115. The needle hub 121 is disposed, for example, outside the proximal end of the handle 103. Inside the handle 103, the needle 107 may be retained in place by retaining members 123. Those skilled in the art will understand that alternate arrangements may be used to retain the needle 107 in conjunction with or in place of retaining members 123.

A stabilization wire 108 is provided, for example, within the stabilization lumen 125. The stabilization wire 108 extends, for example, from a wire base 113 disposed in the handle 103, to a stabilizing element which, in an extended position, protrudes from the distal end of the stabilization lumen 125. In a retracted position, the stabilizing element may be completely received within the stabilization lumen 125, if suitable. In the exemplary embodiment of FIG. 1, the stabilizing element is in the form of a loop 109 which is shaped, for example, as a circular or ovoid wire element which, in an operative position, is placed around an injection site. Loop 109 may be formed, for example, by bending an extension of the stabilization wire 108 back around upon itself and attaching the extension to the stabilization wire 108. Those skilled in the art will understand, however, that any suitable stabilizing element or elements may be used, and that the present invention should not be limited to the embodiments pictured in the Figures and described herein. Likewise, in FIG. 1 the stabilization lumen 125 extends into the handle, but other means of retaining the stabilization wire 108 inside the stabilization lumen 125 may be employed.

In the exemplary embodiment of FIG. 1, needle 107 and stabilization wire 108 are, for example, linked by a linking mechanism, although the linking mechanism may be omitted in other embodiments, including several embodiments described below. When present, the linking mechanism coordinates the movement of the needle 107 and stabilization wire 108 so that as one of the two elements is extended the other of the elements retracts, for example by a corresponding amount. Any suitable linking mechanism may be employed. In the embodiment of FIG. 1, for example, needle base 115 and wire base 113 have teeth extending along inner sides thereof (i.e., the sides facing each other). The teeth interconnect, for example, with gear 117. In this manner, needle base 115, wire base 113, and gear 117 form a rack-and-pinion arrangement that provides smooth, controlled movement of the needle 107 and stabilization wire 108 whereby motion of the needle by a predetermined distance proximally causes a corresponding motion of the stabilization element distally with the ratio of motion being determined based on the distance between the teeth of the needle base 115 as compared to the distance between the teeth of the wire base 113.

At least one of the needle base 115 and the wire base 113 may extend outside the handle 103, or be connected to a component which is outside the handle 103, so that the needle 107 and stabilization wire 108 may be easily manipulated by the operator. In the exemplary embodiment of FIG. 1, the wire base 113 is connected to a control tab 119. The control tab 119 may be shaped, for example, in the form of a thumb loop designed to fit around the thumb of the operator. When the control tab 119 is urged distally by the operator, the stabilization wire 108 (along with the stabilizing element) will extend distally (assuming, for example, that the control tab 119 is attached to the wire base 113). At the same time, if a linking element is present then the needle 107 and needle head 111 will retract, i.e. move proximally, into the needle lumen 127.

Figure 2:
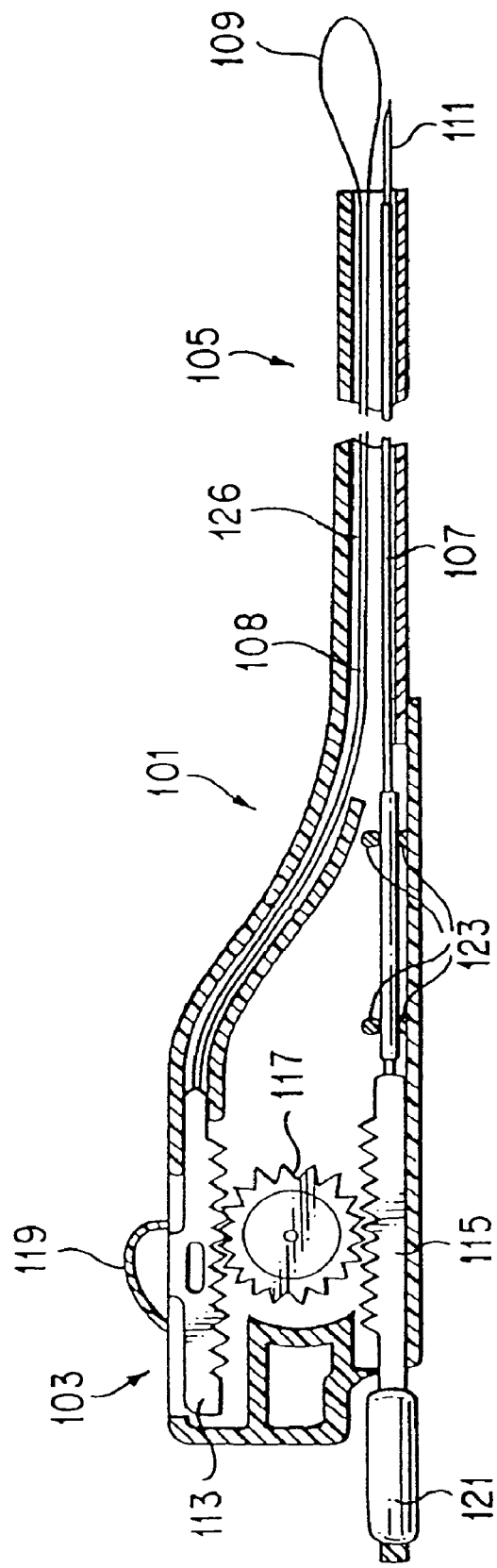
FIG. 2 is a side view of a second exemplary embodiment of an endoscopic needle device according to the present invention.

FIG. 2 illustrates a second exemplary embodiment of a needle device 101 according to the present invention in which only a single lumen is provided. It should be understood that the needle 107 and the stabilization wire 108 need not be maintained in separate lumens. Rather, in certain situations it will be advantageous for the needle 107 and stabilization wire 108 to be located within a single lumen. This may be true, for example, when very narrow vessels or body lumens wherein the profile size of a deployed endoscope may be small, requiring instrumentation and, correspondingly, a catheter sheath 105 having relatively thin cross-sections. As can be seen in FIG. 2, a needle device 101 according to this embodiment of the present invention is similar to the embodiment of FIG. 1. However, the exemplary embodiment of FIG. 2 includes a single lumen 126 in which the needle 107 and stabilization wire 108 are maintained. It may be seen that the catheter sheath 105 of the embodiment of FIG. 2 is of smaller cross-section than the catheter sheath of FIG. 1, but this is not required. In general, the catheter sheath 105 in any embodiment may be of any suitable width. It should also be understood that while the remaining Figures typically illustrate a dual-lumen arrangement, a single-lumen arrangement may be employed with other embodiments of the present invention, including the exemplary embodiments described below.

Figure 3:
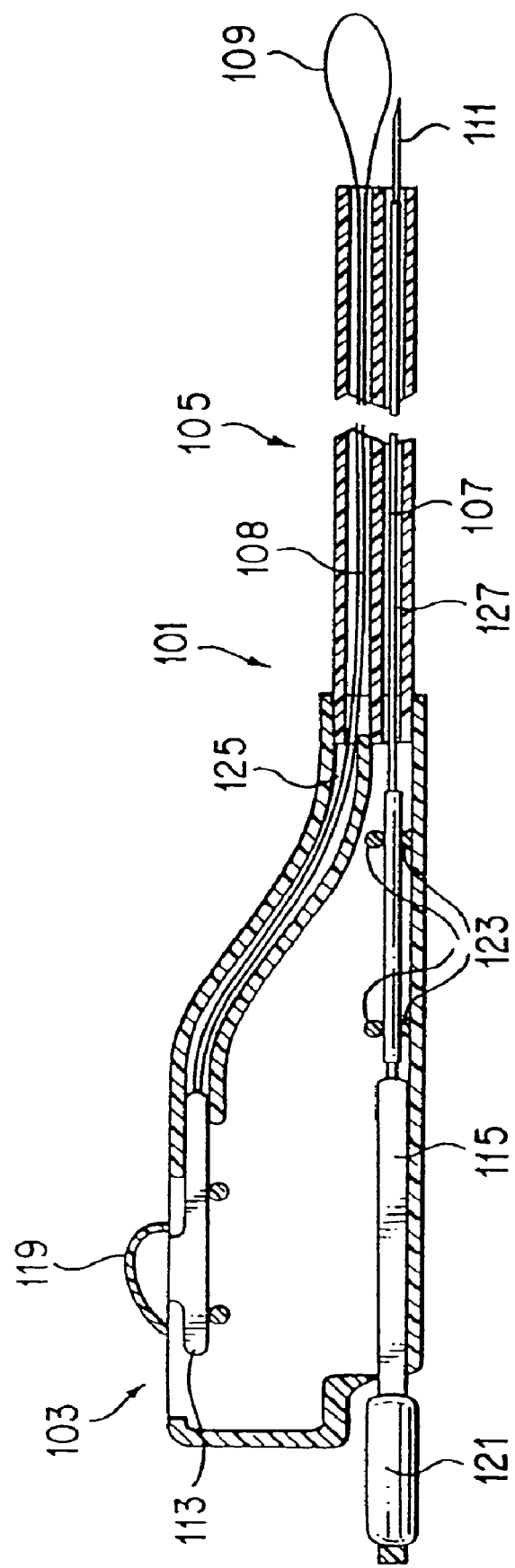
FIG. 3 is a side view of a third exemplary embodiment of an endoscopic needle device according to the present invention.

FIG. 3 illustrates a third exemplary embodiment of a needle device 101 according to the present invention. In this embodiment, movement of the needle 107 and stabilization wire 108 are, for example, not linked. Rather, the needle 107 and stabilization wire 108 may be activated independently, each being movable to any position regardless of the position of the other. Accordingly, needle base 115 and wire base 113 (if present) do not, for example, contain any teeth.

Figure 4:
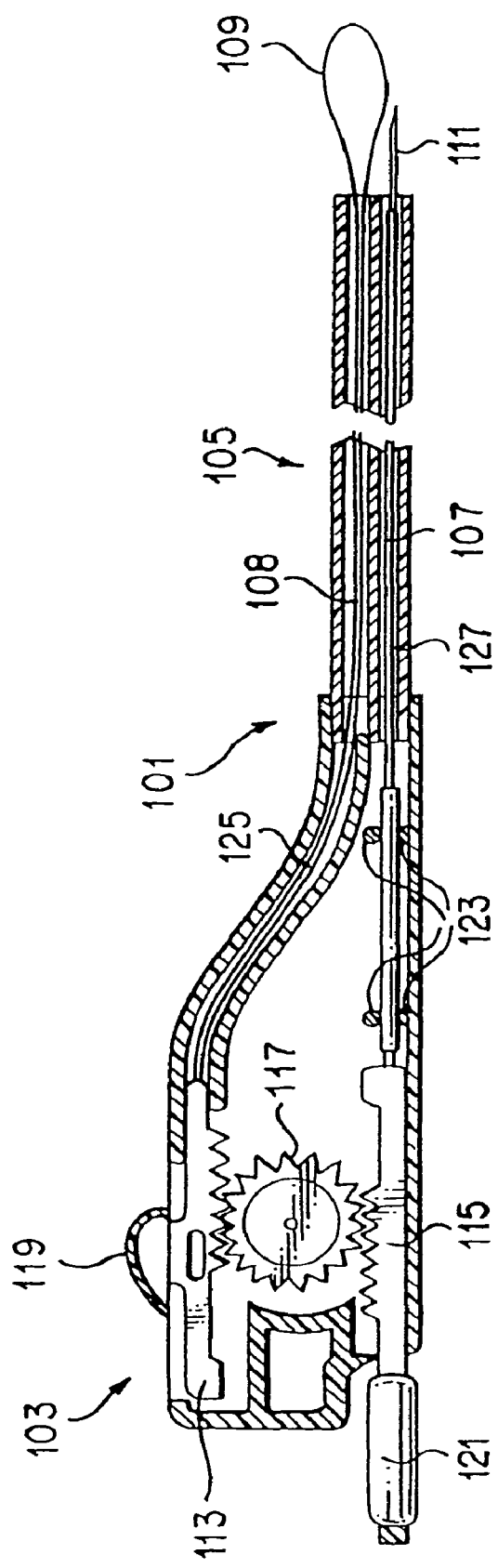
FIG. 4 is a side view of a fourth exemplary embodiment of an endoscopic needle device according to the present invention.

In some situations it may be preferable to provide partial linkage between the needle 107 and stabilization wire 108. In the exemplary embodiment of FIG. 4, for example, the needle base 115 and wire base 113 are provided with teeth along a portion of an inner side. In this manner, stabilization wire 108 can be partially retracted, or needle 107 partially extended, without causing movement of the other member. When the stabilization wire 108 or needle 107 reaches a certain point, however, the teeth of the wire base 113 or needle base 115 contact, for example, gear 117. If the other of the wire base 113 and needle base 115 is also contacting the gear, it will move in the direction opposite movement of the first element.

Figure 5:
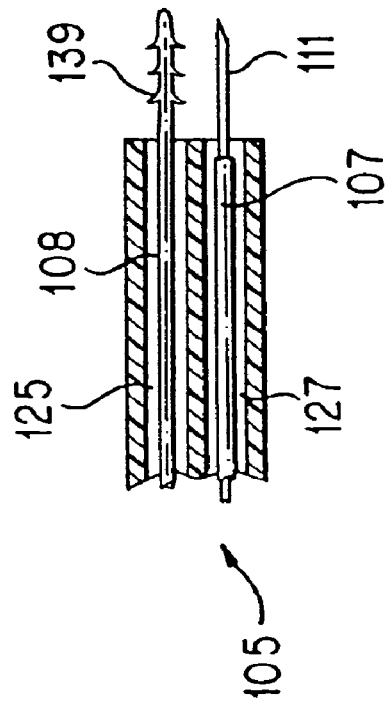
FIG. 5 is a side view of a distal end of the endoscopic needle device of FIG. 1 including a second exemplary embodiment of a stabilization element according to the present invention.
Figure 6:
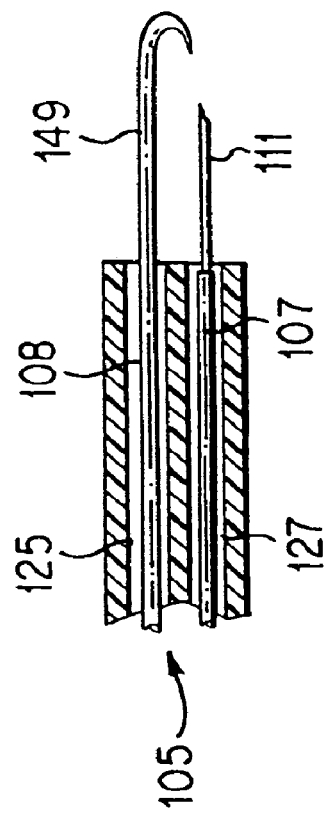
FIG. 6 is a side view of a distal end of the endoscopic needle device of FIG. 1 including a third exemplary embodiment of a stabilization element according to the present invention.

As noted above, any suitable stabilizing element may be employed. FIGS. 5 and 6 illustrate additional embodiments of stabilizing elements that may be used in conjunction with the present invention. FIGS. 5 and 6 each illustrate the distal end portion of a needle device according to the present invention, including, for example, needle lumen 127, needle 107 with needle head 111, stabilization lumen 128, and stabilization wire 108. FIG. 5 illustrates a stabilization element in the shape of a barb 139. The barb 139 may be shaped, for example, as a longitudinal member having one or more backward facing barb elements. The barb 139 may be used, for example, to puncture the injection site. When the stabilization wire 108 and barb 139 are retracted, the barb elements will embed in the site and draw the site towards the needle device 101. Alternatively, the barb 139 may be, for example, scraped against the injection site to draw the site towards the needle device 101.

FIG. 6 illustrates a third exemplary embodiment of a stabilization member according to the present invention. The stabilizing member of FIG. 6 is shaped, for example, as a J-hook 149. The J-hook 149 may be extended, for example, beyond and around an injection site. When retracted, the J-hook 149 will wrap around, and possibly puncture, the injection site, thereby achieving a stable hold on the site. Those skilled in the art will understand that the J-hook 149 may also include one or more barb elements as shown in FIG. 5 to provide additional stabilization.

FIGS. 7 and 8 illustrate the operation of the needle device 101 of FIG. 1 in greater detail. The operation is illustrated with the needle device employing, for example, a loop 109 as the stabilization element. FIG. 7 shows the distal end of the needle device 101 with loop 109 in an extended position placed, for example, around an injection site. Assuming for example that a linkage mechanism is present, with the loop 109 in the extended position, the needle 107 is in a retracted position. In this position, the needle head 111 may be contained entirely within needle lumen 127. However, those skilled in the art will understand that other arrangements may be employed for shielding the needle head 111 while the loop 109 is in the extended position.

Once the stabilization element is in place around the injection site and the site is stabilized, loop 109 may be retracted. When the loop 109 is retracted, as shown in FIG. 8, the injection site is drawn towards the needle device 101. At the same time, the needle 107 extends so that the needle head 111 penetrates the injection site (again assuming linkage). The device may preferably be configured so that when the loop 109 reaches a fully retracted position, the needle reaches a fully extended position, in which the needle head 111 achieves its maximum penetration of the injection site. Once suitable penetration has been achieved, the needle 107 may be retracted (as shown in FIG. 7). Those skilled in the art will understand that the needle 107 and needle head 111 may be extended and retracted numerous times, so that, if desired, the needle head 111 will penetrate the injection site numerous times. The loop 109 may then be withdrawn from around the injection site, and the needle device 101 may be removed.

Accordingly, a method of use of the needle device 101 according to the present invention includes, for example, the following steps. The needle device 101 is inserted and delivered to the injection site. Once the needle device 101 has been positioned at the injection site, the stabilization element is activated to stabilize the site. This may involve looping a loop 109 or J-hook 149 around the site, scraping a barb 139 along the site or thrusting a barb 139 into the site, positioning a grasper around the site (as discussed below), applying a vacuum to the site (as discussed below), or applying some other sort of stabilization element. With the stabilization element activated, the needle may be extended. If a linkage mechanism is present, then the penetration site may be drawn towards the needle device 101 as the needle 107 is extended. Finally, the injection site is penetrated by the needle 107.

Figure 9:
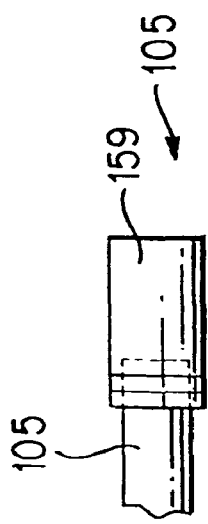
FIG. 9 is a side view of a fifth embodiment of the endoscopic needle device according to the present invention including a fourth exemplary embodiment of a stabilization element according to the present invention.
Figure 10:
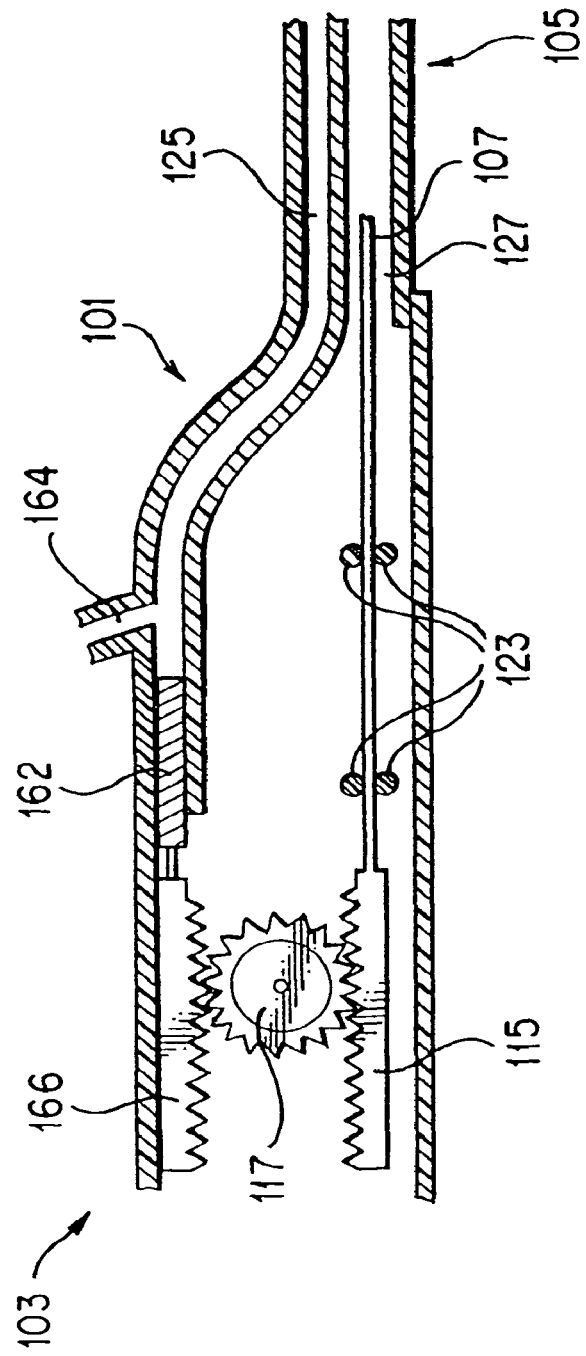
FIG. 10 is a side view of an exemplary embodiment of a valve arrangement and linking mechanism for the needle device of FIG. 9.

FIGS. 9 to 11 illustrate another exemplary embodiment of an endoscopic needle device 101 according to the present invention. In this embodiment, the needle device 101 includes a vacuum hood 159 as the stabilization element. The hood 159 is, for example, a substantially cylindrical member having a substantially cylindrical channel 160 therethrough. The interior diameter of the channel 160 is, for example, substantially equivalent to the outer diameter of catheter sheath 105. The proximal end of the hood 159 may then be placed over the distal end of the endoscopic needle device 101 or the catheter sheath 105, the two members being attached at the overlap section. If desired, the hood 159 may instead be integral with the needle device 101 or catheter sheath 105 rather than a separate, attached member. The hood 159 is arranged, for example, so that the needle head 111 may extend into the channel 160 of the hood 159 when in the extended position.

As shown in FIG. 11, the stabilization lumen 125 of this embodiment need not contain any stabilization wire 108 or stabilization member. Rather, the stabilization lumen 125 may simply be connected to a vacuum (not shown), so that a vacuum can be drawn through the channel 160. The term vacuum is intended to include a partial or full vacuum, as well as any vacuum-creating device, system, or arrangement that may be connected to the stabilization lumen 125 to create a partial or full vacuum therein. The vacuum may be linked to the extension of the needle 107 (for example via a piston or valve arrangement) or may be controlled independently of the needle 107. In either case, the control tab 119 is not connected to the wire base 113 in this embodiment, but instead is connected, for example, to a vacuum base 166 as shown in FIG. 10 or to the needle base 115. The vacuum base 166 may, for example, have the same or substantially the same shape as wire base 113.

An exemplary valve arrangement for connecting the stabilization lumen 125 to a vacuum is shown in FIG. 10. The arrangement includes a vacuum base 166 connected to a piston 162. The vacuum base 166 may be connected to a control tab 119, and may form part of a linking mechanism, as described above with respect to wire base 113. Vacuum base 166 and piston 162 are movable, for example, between extended and retracted positions. In the extended position, the piston 162 blocks vacuum lumen 164 which is connected to a vacuum. Thus in this position no vacuum is established in the stabilization lumen 125 or vacuum hood 159. In the retracted position, however, the piston 162 does not block the vacuum lumen 164. In this position, a vacuum will be established in the stabilization lumen 125 and vacuum hood 159, drawing the injection site into channel 160. Those skilled in the art will understand that the vacuum lumen 164 or the connection between vacuum lumen 164 and stabilization lumen 125 may be shaped (e.g. widened) so that as the piston 162 is retracted a vacuum is gradually established in the stabilization lumen 125 and vacuum hood 159.

In operation, the needle device 101 with vacuum hood 159 is extended to the desired injection site. Once at the site, the vacuum may be applied to draw the injection site into the channel 160, as shown in FIG. 11. As the vacuum is applied, or after the vacuum has been applied, the needle 107 may be extended so that the needle head 111 enters the channel 160 and penetrates the injection site. Once the needle head 111 has adequately penetrated the site, the needle 107 can be retracted and the vacuum terminated. The needle device 101 may then be removed from the site. As in the embodiments described above, it will be understood that the needle head 107 may be extended and retracted a number of times prior to the removal of the needle device 101

FIG. 12 illustrates another exemplary embodiment of a stabilization element in operation. In this embodiment, the stabilization element, generally referred to as a grasper 169, includes, for example, a plurality of longitudinal hook elements 170 extending distally from the needle device 101. The hook elements 170 extend substantially axially from the stabilization wire 108, but in an unbiased position also extend slightly radially outwardly as they extend distally, as shown in FIG. 12. When retracted into the stabilization lumen 125, for example, the hook elements 170 may be forced inwardly so that all of the hook elements 170 fit inside the stabilization lumen 125. When extended outside the stabilization lumen, however, the hook elements may spring back to their slightly outwardly extending position.

The distal tips of hook elements 170 bend back inwardly and proximally, for example, toward the needle device 101. When grasper 169 is extended over an injection site, the hook elements 170 are urged outwardly by the tissue of the injection site. The hook elements 170 therefore exert an inward force on the injection site so that the bent tips of the hook elements 170 frictionally engage or puncture the injection site, as shown in FIG. 12. The grasper 169 may then be retracted to draw the injection site toward the needle device 101. At the same time, needle 107 may be extended until needle head 111 penetrates the injection site. As with the embodiments described above, the needle 107 may be extended and retracted multiple times, if desired. After sufficient penetration has been achieved, the grasper 169 may be separated from the injection site (for example by twisting), and the needle device 101 withdrawn.

Figure 13:
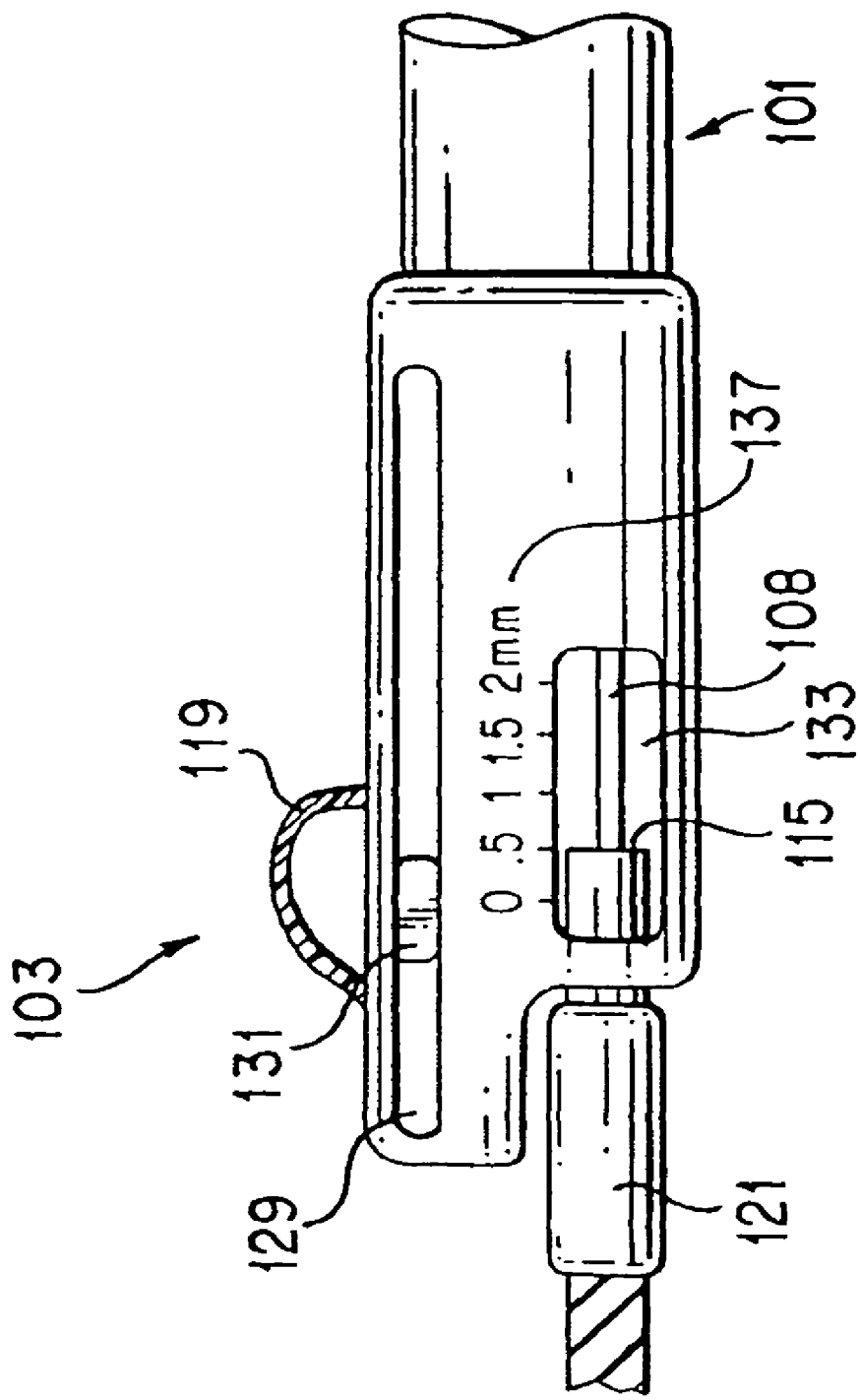
FIG. 13 is a side view of a sixth exemplary embodiment of a needle penetration device according to the present invention having an exemplary embodiment of a needle penetration window according to the present invention.

FIG. 13 illustrates a further exemplary feature of a needle device 101 according to the present invention. In this embodiment, the handle 103 includes, for example, a penetration window 133. The penetration window 133 provides an operator with visual access to, for example, the needle base 115, the needle itself, or another component connected to the needle that may act as a visual depth gauge. In this embodiment, the needle 107 may extend, for example, through a longitudinal channel in the needle base 115 to the needle hub 121. The outer surface of the needle 107 and the inner surface of needle base 115 may be threaded, for example. When the needle hub 121 is rotated, the needle 107 and needle hub 121 move, for example, proximally or distally with respect to the needle base 115, depending on which direction the needle hub 121 is rotated.

In this manner, a maximum penetration depth may be established for the needle head 111. This maximum penetration depth may be adjusted, for example, by rotating the needle hub 121 until the desired depth has been established. The maximum penetration depth may be determined, for example, according to the position of the depth gauge in relation to a set of penetration depth markers 137 appearing on the outside of the handle 103. The depth markers 137 may be arranged so that when the needle 107 is in an initial position, for example the fully retracted position, the position of the needle base 115 relative to the depth markers 137 indicates, for example, the maximum penetration depth of needle head 111.

It may be understood that other arrangements of the needle 107 and the needle hub 121 will allow for adjustment of the needle 107. For example, the needle hub 121 may be fixed to the needle base 115 or handle 103, for example, with respect to the axial direction (i.e. capable of rotational but not axial movement). The needle hub 121 may also include, for example, a channel therethrough having threads on an inner surface that cooperate with threads on a threaded portion of the needle 107. When the needle hub 121 is rotated, the needle 107 will be extended or retracted, thereby altering the maximum penetration depth. This embodiment may or may not include a needle base 115 or other elements described above.

Although the present invention has been described with respect to several exemplary embodiments, those skilled in the art will understand that there are many other variations of the above described embodiments within the teaching of the present invention, which is to be limited only by the claims appended hereto.

What is claimed is:

1. A method of injecting a needle into an injection site, comprising:
    inserting a needle device into a body, the needle device including:
        a handle;
        a catheter sheath connected to the handle, the catheter sheath having a longitudinal axis;
        a stabilization element disposed at the distal end of the needle device, the stabilization element having a longitudinal axis; and
        a needle disposed at the distal end of the needle device, the needle having a longitudinal axis,
        wherein the longitudinal axis of the stabilization element is parallel to the longitudinal axis of the needle, and
        wherein the longitudinal axis of the stabilization element and the longitudinal axis of the needle are both offset from the longitudinal axis of the catheter sheath;
    delivering a distal end of the needle device to an injection site; and adjusting at least one of the stabilization element and the needle to control penetration of the tissue at the injection site by the needle while using the stabilization element to hold the tissue at the injection site, wherein the step of adjusting the needle to control the penetration of the tissue comprises rotating a needle hub engaged with a surface of the needle.

2. The method according to claim 1, wherein the needle hub includes a threaded surface for engaging an outer surface of the needle that is threadably coupled to the threaded surface.

3. The method according to claim 2, wherein rotating the needle hub in a first direction moves the needle distally to increase the depth of the penetration of the needle; and wherein rotating the needle hub in a second direction opposite the first direction moves the needle proximally to decrease the depth of the penetration of the needle.

4. The method according to claim 1, further comprising determining the depth of the penetration of the tissue at the injection site by the needle and adjusting one of the stabilization element and the needle based on the depth of penetration of the tissue at the injection site.

5. The method according to claim 1, wherein the step of adjusting one of the stabilization element and the needle over at least a part of a range of movement in a first direction causes the other of the stabilization element and the needle to move in a second direction opposite the first direction.

6. A method of injecting a needle into an injection site, comprising:
    inserting a needle device into a body, the needle device including:
        a handle;
        a catheter sheath connected to the handle, the catheter sheath having a longitudinal axis;
        a stabilization element disposed at the distal end of the needle device, the stabilization element having a longitudinal axis; and
        a needle disposed at the distal end of the needle device, the needle having a longitudinal axis,
        wherein the longitudinal axis of the stabilization element is parallel to the longitudinal axis of the needle, and
        wherein the longitudinal axis of the stabilization element and the longitudinal axis of the needle are both offset from the longitudinal axis of the catheter sheath;
    delivering a distal end of the needle device to an injection site;
    applying the stabilization element to hold tissue at the injection site;
    penetrating tissue at the injection site with the needle while using the stabilization element to hold the tissue at the injection site; and
    determining the depth of the penetration of the tissue at the injection site by the needle using a measurement mechanism.

7. The method according to claim 6, wherein the measurement mechanism is a depth gauge.

8. The method according to claim 7, wherein the step of determining the depth of penetration of the tissue at the injection site comprises determining the depth of penetration based on the position of the depth gauge in relation to depth markers located on the handle.

9. The method according to claim 6, further comprising adjusting at least one of the stabilization element and the needle to control the penetration of the tissue at the injection site by the needle, based on the determination of the depth of penetration of the tissue at the injection site.

10. The method according to claim 9, wherein the step of adjusting the needle to control the penetration of the tissue comprises rotating a needle hub coupled to the needle in a first direction to increase the depth of the penetration of the needle; and rotating the needle hub in a second direction opposite the first direction to decrease the depth of the penetration of the needle.

11. The method according to claim 9, wherein the step of adjusting the stabilization element to control penetration of the tissue comprises actuating a control tab.

12. A method of injecting a needle into an injection site, comprising:
  inserting a needle device into a body, the needle device including:
    a handle,
    a catheter sheath connected to the handle, the catheter sheath having a longitudinal axis;
    a needle at least partially disposed within the catheter sheath and axially movable relative to the catheter sheath, the needle having a longitudinal axis; and
    a stabilization mechanism for holding tissue at an injection site, the stabilization mechanism having a longitudinal axis,
  wherein the longitudinal axis of the needle is parallel to the longitudinal axis of the stabilization mechanism, and
  wherein the longitudinal axis of the stabilization mechanism and the longitudinal axis of the needle are both offset from the longitudinal axis of the catheter sheath;
  delivering a distal end of the needle device to the injection site;
  stabilizing tissue at the injection site; and
  controlling penetration of tissue at the injection site by the needle,
  wherein the step of controlling penetration of tissue comprises drawing the injection site towards the catheter sheath while simultaneously extending the needle distally relative to the catheter sheath to penetrate tissue at the injection site.

13. A method of injecting a needle into an injection site, comprising:
  inserting a needle device into a body, the needle device including:
    a handle,
    a catheter sheath connected to the handle, wherein the catheter sheath has a longitudinal axis;
    a needle at least partially disposed within the catheter sheath and axially movable relative to the catheter sheath, the needle having a longitudinal axis; and
    a stabilization mechanism for holding tissue at an injection site, the stabilization mechanism having a longitudinal axis,
  wherein the longitudinal axis of the needle is parallel to the longitudinal axis of the stabilization mechanism, and
  wherein the longitudinal axis of the stabilization mechanism and the longitudinal axis of the needle are both offset from the longitudinal axis of the catheter sheath;
  delivering a distal end of the needle device to the injection site;
  stabilizing tissue at the injection site;
  controlling penetration of tissue at the injection site by the needle, and
  monitoring the depth of penetration of tissue at the injection site by the needle.

14. The method according to claim 13, wherein the handle includes a depth gauge for indicating the depth of penetration of the tissue at the injection site and a window for visualizing the depth gauge, and further comprising determining the depth of penetration based on a position of the depth gauge within the window.

15. The method according to claim 14, wherein the step of controlling penetration of tissue comprises adjusting the position of the needle relative to the sheath based on the determination of the depth of penetration.

* * * * *